United States Patent [19]
Nelson et al.

[11] Patent Number: 5,586,557
[45] Date of Patent: Dec. 24, 1996

[54] FUNCTIONAL AMBULATION PERFORMANCE SCORING DEVICE

[75] Inventors: Arthur J. Nelson, New York; Clifford M. Gross, Roslyn, both of N.Y.

[73] Assignee: BCAM International, Inc., Melville, N.Y.

[21] Appl. No.: 251,596
[22] Filed: May 31, 1994
[51] Int. Cl.⁶ ............................................. A61B 5/103
[52] U.S. Cl. .................................................. 128/779
[58] Field of Search ............................... 128/774, 779, 128/782; 73/172; 36/136

[56] References Cited

U.S. PATENT DOCUMENTS

| | | | |
|---|---|---|---|
| 2,290,387 | 7/1942 | Schwartz | 128/779 |
| 4,152,748 | 5/1979 | Arkans | 128/779 |
| 4,503,705 | 3/1985 | Polchaninoff | 128/779 |
| 4,745,930 | 5/1988 | Confer | 128/779 |
| 5,323,650 | 6/1994 | Fullen et al. | 128/779 |
| 5,357,696 | 10/1994 | Gray et al. | 128/779 |

*Primary Examiner*—Max Hindenburg
*Attorney, Agent, or Firm*—Snell & Wilmer L.L.P.

[57] ABSTRACT

A device comprising a system of switches and sensors placed inside a person's footgear which send positional information through wireless telemetry from a transmitter to a receiver. This positional information is entered into a computer and processed according to prestored algorithms, yielding a non-dimensional ambulation index. This invention also comprises a method for calculating the non-dimensional ambulation index.

18 Claims, 2 Drawing Sheets

FUNCTIONAL AMBULATION PERFORMANCE SCORING DEVICE

BACKGROUND OF THE INVENTION

1. Field of the Invention

This invention relates to devices used in examining human ambulation and more particularly to devices that help analyze and quantitatively evaluate human ambulation.

2. Description of the Prior Art

In clinical applications, there is an ongoing need to analyze and evaluate human ambulation. Clinicians often use such information to evaluate patient health status and recuperation following treatment, such as, drug therapy, rehabilitation, and surgery.

In the prior art, human gait has been traditionally an observational procedure that qualitatively assesses a number of factors in gait but does not formulate a quantitative measure of gait. There has been a number of methods of measuring gait by videotaping and subsequently analyzing the movement of the person three- or two-dimensionally in what is called a kinematic analysis. This also does not provide an ambulation score or unitary value of locomotion.

Another approach to human gait analysis has employed the measurement of pressure gradients from the plantar surface of the feet. There are several instruments that provide this information, such as F-scan and the electrodynograph. These also do not provide a score or quantification of human ambulation performance.

Thus, the prior art lacks equipment to easily, quickly, and economically evaluate human ambulation, and methods to perform a quantitative analysis of human ambulation.

SUMMARY OF THE INVENTION

A primary object of the instant invention is a device designed to gather data on human ambulation for further processing into a non-dimensional ambulation index.

Another object of this invention is a portable and lightweight human ambulation measuring device.

Another object of this invention is a human ambulation measuring device that can interface with a microcomputer.

Still another object of this invention is a non-dimensional ambulation index.

In short, this invention comprises a system of switches and sensors placed inside a person's footgear which send positional information through wireless telemetry from a transmitter to a receiver. This positional information is entered into a computer and processed according to pre-stored algorithms, yielding a non-dimensional ambulation index. This invention also comprises a method for calculating the non-dimensional ambulation index.

DESCRIPTION OF PREFERRED EMBODIMENT

Figure 1:
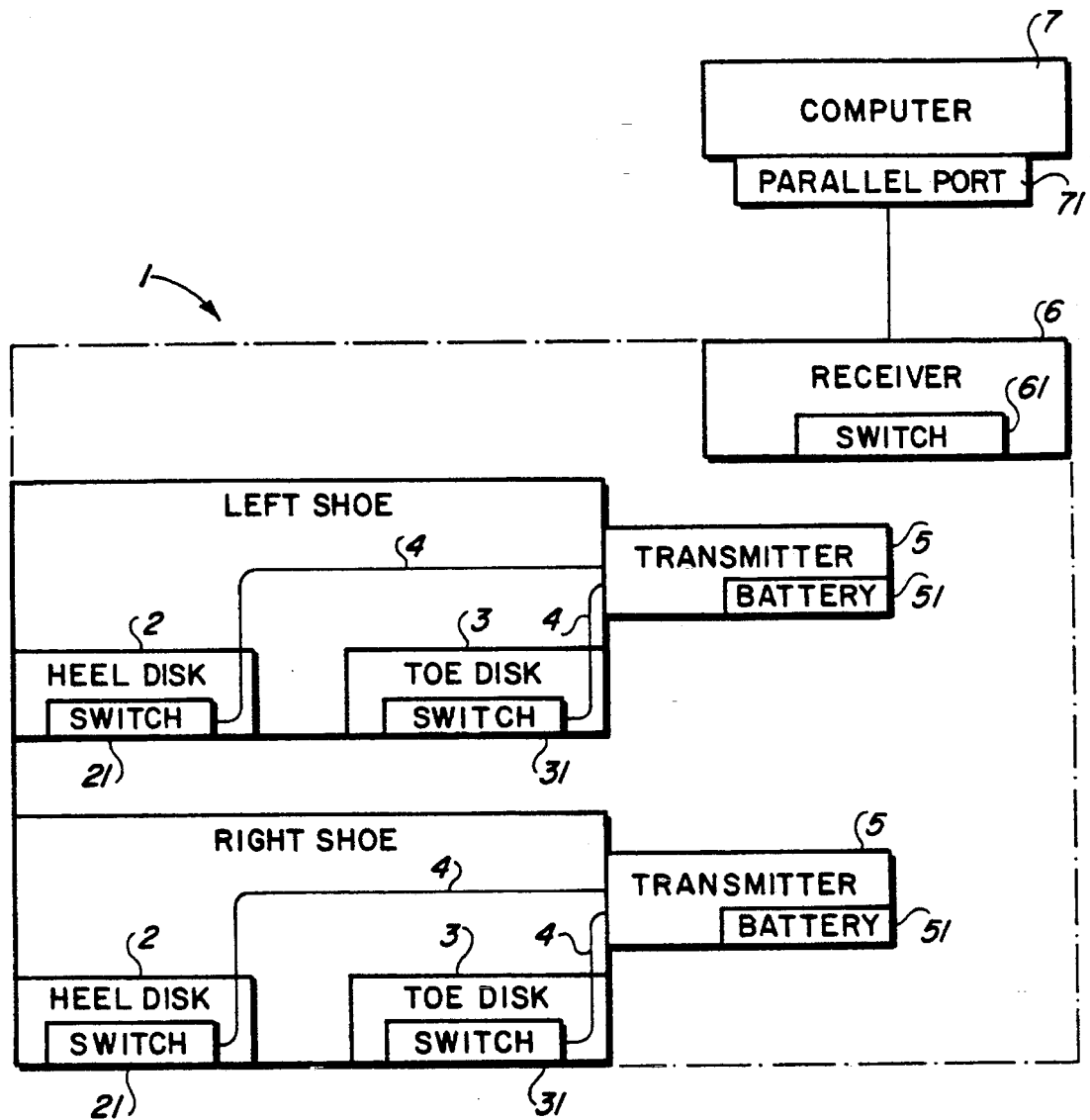
FIG. 1 is a block diagram of the gait measuring device.

In its preferred embodiment, the device 1 is a system comprising two sets of a heel disk 2 and a toe disk 3 which are placed on top of the inner sole of each shoe or other footgear worn by a person. The heel disk 2 is removably but securely attached to the inner sole at approximately the location of the person's heel using any one of the many well-known removable adhesives, such as rubber cement. The heel disk 2 has an "on-off" heel switch 21 which has a sensitivity allowing it to be compressed, and thereby activated by the pressure typically applied under a person's heel during ambulation. Preferably, the heel switch 21 is a well-known micro-dome switch which is readily obtainable.

Similarly, the toe disk 3 is removably but securely attached to the inner sole at approximately the location of the ball of the foot using the same kind of adhesive. The toe disk 3 has an "on-off" toe switch 31 which has a sensitivity allowing it to be compressed, and thereby activated by the pressure typically applied under the ball of the foot during ambulation. Preferably, the toe switch 31 is also a microdome switch.

Thin flexible wire 4 connects each of these switches 21, 31 to a miniature RF transmitter 5 which is removably attached to the outside of each shoe. The preferable attachment means is a hook-and-fastener combination, which allows for easy attachment, removal, and reattachment when the device 1 is not needed or may be damaged due to exposure to rain, mud, or other environmental conditions. The transmitter 5 has a replaceable battery 51 to provide the necessary power. Preferably, this transmitter is similar to the wireless transmitters commonly used in automobile alarms.

Thus, corresponding to each foot is a set of disks, wire, and transmitter.

The target of transmissions from the two transmitters 5 is a single receiver 6 which is connected to a microcomputer 7 via the computer's parallel port 71. The receiver 6 is preferably a commonly available RF receiver. The receiver 6 has an on/off switch 61 that controls receipt of transmissions from the transmitters 5.

In use, a clinician measures the distance between the patient's greater trochanter and the ground for both the patient's left side ("Left-Side Greater Trochanter") and right side ("Right-Side Greater Trochanter").

The clinician attaches the disks 2, 3 to the soles of the shoes and the transmitters 5 to the outside of the shoes. The clinician then determines the distance between the heel and toe disks in each of the patient's shoes.

The on/off switch 61 is set to "on". Because the patient's feet are initially flat on the floor, all four microswitches 21, 31 are activated from the weight of the patient. Each wire 4 carries a signal to the corresponding transmitter 5 which indicates that each microswitch 21, 31 is activated. The transmitters 5 send these initial transmissions to the receiver 6, which relays these transmissions to the computer 7 via the parallel port 71. Using standard and well-known telemetry algorithms prestored in the computer 7, the computer 7 internally represents the initial position for the patient's feet and, based upon the computer's internal clock, an initial time. The patient then walks a distance preset between 3 and 6 meters.

During the walking process, when a portion of a foot near any microswitch 21, 31 is not on the ground, there will be insufficient pressure on that microswitch 21, 31 to activate it. As any such foot portion is placed on the ground, the pressure then on the corresponding microswitch 21, 31 will activate it. Each microswitch, upon activation, induces the wire 4 to carry a signal to the corresponding transmitter 5 indicating that that microswitch 21, 31 is currently activated; this signal continues as long as that microswitch remains activated. The transmitters 5 transmit a signal to the receiver 6 which indicates the specific microswitch 21, 31 that is currently activated; this transmission continues as long as that microswitch remains activated.

The microswitch 21, 31 continues to be activated as long as there is pressure on it. The duration of the activation corresponds to the stance phase—the time period during which the corresponding foot is supporting the body above it. The duration of the non-activation corresponds to the swing phase—the time period during which the corresponding foot is swinging or free from the walking surface.

The receiver 6 relays this information to the computer 7 via the parallel port 71. Using standard and well-known telemetry algorithms prestored in the computer 7, the computer 7, having the transmissions from corresponding heel and toe microswitches 21, 31, can determine the current position of that foot relative to the initial position of the patient's feet and, based upon the computer's internal clock, the corresponding time.

Based upon these positional and time readings, the computer 7 determines the duration of the walk and the number of steps taken over the preset distance. The computer 7 then utilizes standard and well-known prestored algorithms to calculate velocity, cadence, average one-step distance from left heel to right heel ("Left-Step Length"), and average one-step distance from right heel to left heel ("Right-Step Length").

Further calculations then occur. First are calculated a Left-Step ratio (Left-Step Length/Left-Side Greater Trochanter), and a Right-Step ratio (Right-Step Length/Right-Side Greater Trochanter). Next, velocity and cadence are then used in well-known prestored algorithms to calculate an average Left-Step time and an average Right-Step time. The Left-Step ratio is then adjusted by qualitatively comparing it to the Left-Step Time; similarly, the Right-Step ratio is adjusted by qualitatively comparing it to the Right-Step Time.

Figure 2:
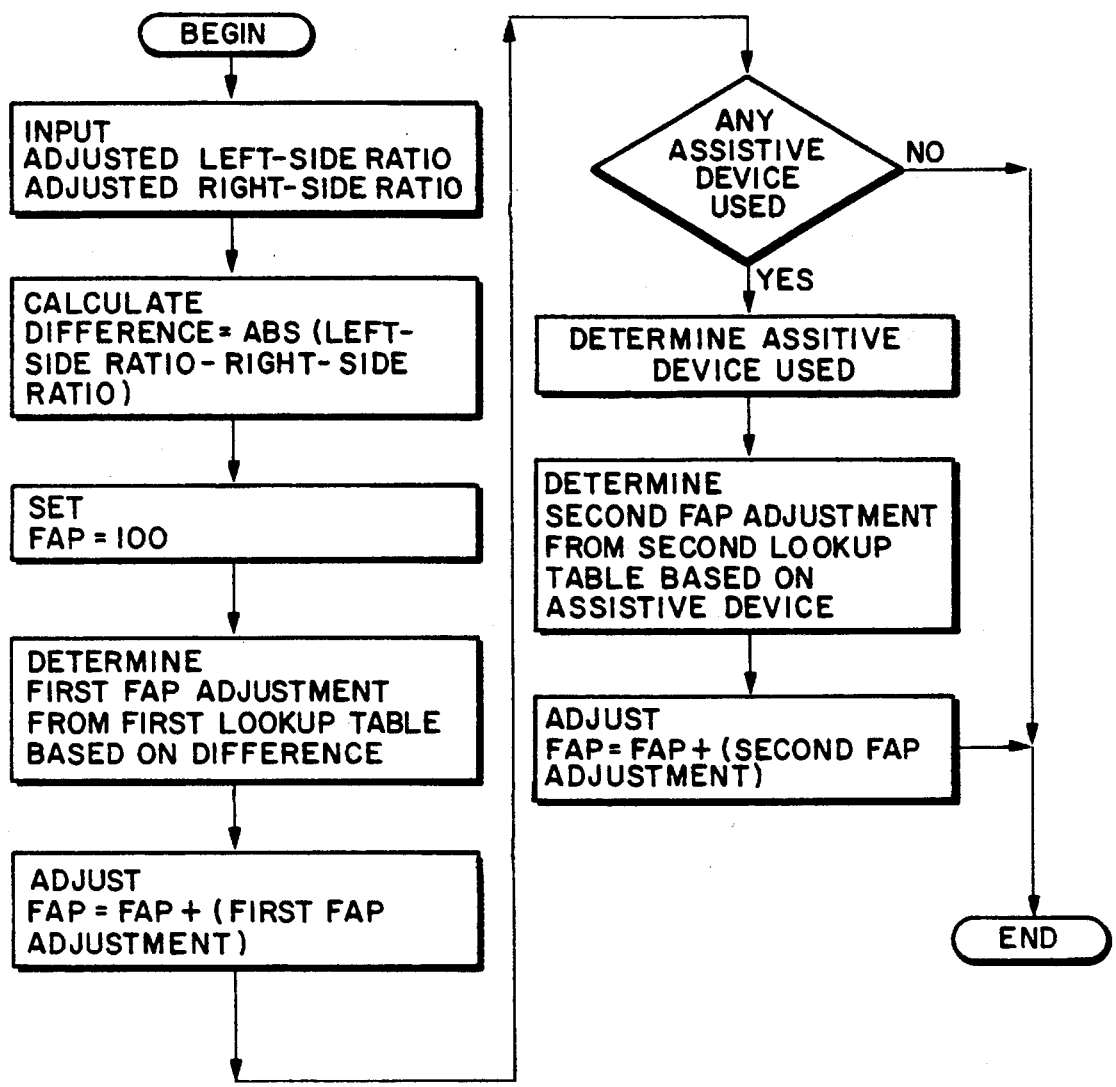
FIG. 2 is a flow chart of a processing algorithm used in calculating a non-dimensional ambulation index.

At this point, an algorithm as set forth in FIG. 2 then determines a Functional Ambulation Performance score ("FAP") for that patient. The FAP is initially set at 100 points. Then, utilizing a prestored look-up adjustment table, the FAP is adjusted. The preferred look-up table is as follows:

| If the difference between Left-Step and Right-Step is: | Adjust the FAP by: |
| --- | --- |
| less than 1.0 cm | 0 points |
| 1.0 cm to 1.9 cms | 5 points |
| 2.0 cms to 2.9 cms | 10 points |
| 3.0 cms to 3.9 cms | 15 points |
| 4.0 cms to 4.9 cms | 20 points |
| 5.0 cms to 5.9 cms | 25 points |
| 6.0 cms to 6.9 cms | 30 points |
| 7.0 cms to 7.9 cms | 35 points |
| 8.0 cms or more | 40 points |

This adjusted FAP is displayed on the computer's output device for the clinician's information. Finally, the clinician makes a final adjustment to the FAP based upon the observed condition of the patient. The preferable adjustments are as follows:

| Type of Assistive Device used by the subject: | Adjust the FAP by: |
| --- | --- |
| Orthoses or prosthesis | 5 points |
| Walking (cane, crutches) | 5 points |
| Personal assistance | 5 points |
| Requires guarding* | 5 points |
| Dependent | 5 points |

*requires verbal guidance but no physical contact.

Although this invention has been described with a certain degree of particularity, it is to be understood that the present disclosure has been made only by way of illustration and that numerous changes in the details of construction and arrangement of parts may be resorted to without departing from the spirit and scope of this invention.

We claim:

1. For use with a walking surface and left and right feet, a device for measuring human ambulation comprising:

(a) a left foot sensor capable of sensing when the left foot is in contact with the walking surface, the left foot sensor being activated when such contact occurs;

(b) a right foot sensor capable of sensing when the right foot is in contact with the walking surface, the right foot sensor being activated when such contact occurs;

(c) a processor having an algorithm to create an ambulation index reflective of a quantitative analysis of human ambulation;

(d) left transmission means for indicating to the processor when the left foot sensor is activated;

(e) right transmission means for indicating to the processor when the right foot sensor is activated; and (f) output means to output the ambulation index from the processor.

2. A device for measuring human ambulation as described in claim 1 in which each of the left and right transmission means comprises a wireless transmitter, a wireless receiver, and an input port to the processor.

3. A gait measuring system comprising:

a first assembly configured to evidence an on mode and an off mode, said first assembly being in said on mode when pressure is applied to said first assembly;

a second assembly configured to evidence an on mode and an off mode, said second assembly being in said on mode when pressure is applied to said second assembly;

a timing device for comparing the time between said first and second assemblies being in said on and off modes and calculating time differentials therefrom; and, a processor configured to utilize said time differentials to calculate a gait measurement.

4. The system of claim 3 wherein each of said first and second assemblies comprises first and second electrical contact switches.

5. The system of claim 4 wherein said first assembly first switch is connected to a rear portion of a subject's first shoe and said second assembly first switch is connected to a rear portion of a subject's second shoe.

6. The system of claim 5 wherein said first assembly second switch is connected to a front portion of said subject's first shoe and said second assembly second switch is connected to a front portion of said subject's second shoe.

7. The system of claim 6 further comprising transmission means for transmitting information representative of the mode of each of said assemblies and receiver means for receiving said information from said transmission means, said receiver means communicating with said timing device.

8. An ambulation measuring system comprising:

first and second contact switches connected to a subject's first shoe, each switch evidencing an on state when pressure is applied to such switch;

third and fourth contact switches connected to a subject's second shoe, each switch evidencing an on state when pressure is applied to such switch; and, a computer configured to communicate with said switches, said computer including a clock and a gait measurement index;

wherein, said computer and said clock are configured to calculate a current position of a subject's foot relative to said subject's initial feet position, and a corresponding time, by utilizing said gait measurement index;

further wherein, said computer is configured to calculate duration of ambulation and number of steps taken over a preset distance based upon said predetermined positional and time calculations.

9. The system of claim 8 wherein said first switch is connected to a rear portion of said subject's first shoe and said third switch is connected to a rear portion of said subject's second shoe.

10. The system of claim 9 wherein said second switch is connected to a front portion of said subject's first shoe and said fourth switch is connected to a front portion of said subject's second shoe.

11. The system of claim 8 wherein said gait measurement index comprises a right side trochanter measurement and a left side trochanter measurement.

12. An ambulation measurement system for use in measuring the ambulation of a subject, the subject having first and second legs and first and second footwear appliances configured for attachment to the lower end of the subject's first and second legs, the system comprising:

a first assembly configured for placement in the subject's first footwear appliance, said first sensing assembly evidencing a first mode and a second mode and being configured for fluctuation between said first and second modes;

a second sensing assembly configured for placement in the subject's second footwear appliance, said second sensing assembly evidencing a first mode and a second mode and being configured for fluctuation between said first and second modes; and, a processor including a clock and configured for receipt and use of information reflective of said mode of said first and second assemblies and time information associated with said fluctuation between said modes;

wherein said system is configured to provide output associated with said subject's ambulation.

13. The system of claim 12 wherein said first sensing assembly comprises a first contact switch connected to a rear portion of said subject's first footwear appliance.

14. The system of claim 13 wherein said first sensing assembly further comprises a second contact switch connected to a front portion of said subject's first footwear appliance.

15. The system of claim 14 wherein said second sensing assembly comprises a first contact switch connected to a rear portion of said subject's second footwear appliance.

16. The system of claim 15 wherein said second sensing assembly further comprises a second contact switch connected to a front portion of said subject's second footwear appliance.

17. The system of claim 16 further comprising transmission means for transmitting information representative of the mode of each of said sensing assemblies and receiver means for receiving said information from said transmission means, said receiver means communicating with said processor.

18. The system of claim 17 wherein each of said contact switches comprises an electrical contact switch.

\* \* \* \* \*